United States Patent
Wang et al.

(10) Patent No.: US 9,880,614 B2
(45) Date of Patent: Jan. 30, 2018

(54) WEARABLE ELECTRONIC DEVICE CAPABLE OF CHANGING APPEARANCE AND OPERATING METHOD THEREOF

(71) Applicant: MediaTek Inc., Hsin-Chu (TW)

(72) Inventors: Tsung-Te Wang, Taipei (TW); Yi-Kai Lee, New Taipei (TW)

(73) Assignee: MEDIATEK INC., Hsin-Chu (TW)

( * ) Notice: Subject to any disclaimer, the term of this patent is extended or adjusted under 35 U.S.C. 154(b) by 143 days.

(21) Appl. No.: 14/821,136

(22) Filed: Aug. 7, 2015

(65) Prior Publication Data

US 2017/0038827 A1    Feb. 9, 2017

(51) Int. Cl.
| | |
|---|---|
| G06F 3/01 | (2006.01) |
| A61B 5/16 | (2006.01) |
| A61B 5/00 | (2006.01) |
| G06F 1/16 | (2006.01) |

(52) U.S. Cl.
CPC ............... G06F 3/01 (2013.01); A61B 5/16 (2013.01); A61B 5/6824 (2013.01); G06F 1/163 (2013.01); G06F 1/1647 (2013.01); G06F 1/1652 (2013.01)

(58) Field of Classification Search
CPC .......... G06F 3/01; G06F 1/163; G06F 1/1647; G06F 1/1652; A61B 5/16; A61B 5/6824
See application file for complete search history.

(56) References Cited

U.S. PATENT DOCUMENTS

| | | | | |
|---|---|---|---|---|
| 5,881,787 | A * | 3/1999 | Davis | A45C 13/1069 150/103 |
| 7,751,285 | B1 | 7/2010 | Cain | |
| 7,969,478 | B1 * | 6/2011 | Chen | H04N 5/58 348/223.1 |
| 9,020,443 | B1 * | 4/2015 | Tyler | H04B 17/318 455/115.4 |
| 9,288,836 | B1 * | 3/2016 | Clement | H04W 84/18 |
| 2007/0183021 | A1 * | 8/2007 | Huang | G02F 1/167 359/296 |
| 2008/0246602 | A1 * | 10/2008 | Aaron | H04W 8/183 340/539.13 |
| 2010/0234714 | A1 | 9/2010 | Mercier et al. | |
| 2010/0332553 | A1 * | 12/2010 | Choi | G06F 17/30256 707/802 |
| 2013/0076936 | A1 * | 3/2013 | Yoshida | H04N 5/23293 348/222.1 |

(Continued)

FOREIGN PATENT DOCUMENTS

CN    202196273 U  *  4/2012  ............. G04B 45/00

*Primary Examiner* — Larry Sternbane
(74) *Attorney, Agent, or Firm* — McClure, Qualey & Rodack, LLP

(57) ABSTRACT

An operating method for controlling a wearable electronic device is provided. The operating method obtains an environmental variable (which is indicative of the current environment) and determines an appearance variable (e.g., a user's favorite color) based on the environment variable, by referring to information about different appearances predetermined to be suitable for different environmental conditions. The operating method also generates a control signal for adjusting the appearance of at least one non-panel region of the wearable electronic device based on the appearance variable. This causes the adjusted appearance of the non-panel region of the wearable electronic device to change based on the current environment.

48 Claims, 8 Drawing Sheets

(56) References Cited

U.S. PATENT DOCUMENTS

2013/0222270 A1    8/2013  Winkler et al.
2015/0187327 A1    7/2015  Francis et al.
2016/0299360 A1*  10/2016  Fonte .................... G02C 7/028

* cited by examiner

WEARABLE ELECTRONIC DEVICE CAPABLE OF CHANGING APPEARANCE AND OPERATING METHOD THEREOF

BACKGROUND OF THE INVENTION

Field of the Invention

The disclosure generally relates to a wearable electronic device, and more particularly, to an operating method for controlling the appearance of the wearable electronic device.

Description of the Related Art

Wearable electronic devices which provide certain functions such as communication and healthcare are getting more popular nowadays. Specifically, a wearable electronic device is not only a machine but also an accessory, since it may be worn by a user on the body, mostly on the wrist or head. As such, it plays an important decorative or ornamental and lifestyle role for the user. When the user wears the wearable electronic device every day for communications or healthcare purposes, it becomes a problem when the wearable electronic device is not always suitable for the occasion or does not match the user's clothing/accessory. Putting on another dress or purchasing another wearable electronic device is not a convenient solution to this problem.

Therefore, there is a continuing need for wearable electronic devices with appearances meeting conditions of different environments where the wearable electronic device is located.

BRIEF SUMMARY OF THE INVENTION

The disclosure proposes an operating method for controlling a wearable electronic device. The operating method can adjust the appearance of the wearable electronic device based on at least one condition of the current environment of the wearable electronic device. The operating method can solve the aforementioned problem.

More specifically, the appearances of the wearable electronic device and/or another wearable electronic device can be determined and adjusted according to the detected environment variable. The operating method can be configured to change the appearance of the wearable electronic device in association with the current environment in real-time. In addition, a database could be predefined and embedded in or accessible to the wearable electronic device to record the preference of users and other information. The suggested appearance of the wearable electronic device can be determined according to the database, the detected environment variable and/or the selection of users. Therefore, there is no need to put on another dress or change to wear another wearable electronic device for adjusting and changing the appearance of the wearable electronic device.

In one aspect of the disclosure, an operating method for controlling a wearable electronic device is provided. The operating method can include obtaining at least one environment variable of the current environment of the wearable electronic device, determining at least one appearance variable based on the at least one environment variable by referring to information about different appearances predetermined to be suitable for different environmental conditions, and generating a first control signal for adjusting the appearance of at least one non-panel region of the wearable electronic device according to the at least one appearance variable so that the adjusted appearance of the at least one non-panel region of the wearable electronic device is adapted to a condition of the current environment. Preferably but not limitedly, the at least one environment variable may comprise at least one temporal variable, at least one spatial/location variable, at least one light variable, at least one occasion variable, at least one user biological variable, and/or at least one air condition variable. In addition, the at least one temporal variable may comprise a date variable, a time variable, a year variable, a month variable, and a day variable.

In some embodiments of the disclosure, the different appearances predetermined to be suitable for the different environmental conditions include at least one preferred or suitable or preconfigured appearance predetermined to be suitable for at least one specific date. Preferably but not limitedly, the different appearances predetermined to be suitable for the different environmental conditions can comprise different lucky colors predetermined to be suitable for different dates or time periods determined according to the birthday, birth month, or birth year of the user. The at least one environment variable may comprise at least one clothing/accessory variable of the user. The at least one clothing/accessory variable of the user may comprise at least one color of the clothing/accessory of the user and/or at least one pattern of the clothing/accessory of the user. Furthermore, the different appearances predetermined to be suitable for the different environmental conditions may comprise different colors and/or patterns matching different colors of the clothing/accessory of the user and/or different clothing/accessory patterns of the user.

In some embodiments of the disclosure, the at least one environment variable comprises at least one social occasion variable. Preferably but not limitedly, the different appearances predetermined to be suitable for the different environmental conditions may include different colors and/or patterns suitable for different social occasions. In addition, the at least one environment variable may comprise at least one environment brightness variable. The different appearances predetermined to be suitable for the different environmental conditions may comprise different contrasts suitable for different environment brightness values.

In some other embodiments of the disclosure, the step of determining the at least one appearance variable is further based on the at least one non-environmental variable. The at least one non-environmental variable may comprise at least one user-selection variable. Preferably but not limitedly, the operating method further includes providing a plurality of candidate appearances predetermined to be suitable for the condition of the current environment, displaying a plurality of options for suggesting the one or more candidate appearances on a display region of the wearable electronic device to be selected by a user; and, and obtaining the at least one user-selection variable according to the result of a selection made by the user.

In some embodiments of the disclosure, the operating method further includes detecting the current environment of the wearable electronic device, and the at least one environment variable of the current environment of the wearable electronic device is obtained from the results of the detection.

In some embodiments of the disclosure, the different appearances predetermined to be suitable for different environmental conditions can be predefined by the user. The different appearances predetermined to be suitable for different environmental conditions may be obtained from a look-up table. In addition, the information defining the different appearances predetermined to be suitable for the different environmental conditions can be updated by an auto-learning mechanism.

In some embodiments of the disclosure, the step of obtaining the at least one environment variable of the current environment of the wearable electronic device can include capturing at least one image of the current environment, and extracting the at least one environment variable from the captured image(s). In addition, the step of obtaining the at least one environment variable of the current environment of the wearable electronic device can include sensing the current environment by at least one sensor to obtain sensing data, and extracting the at least one environment variable of the current environment from the sensing data.

In some embodiment of the disclosure, the operating method further includes detecting whether at least one other wearable electronic device is connected to the wearable electronic device, and generating a second control signal for adjusting the appearance of at least one non-panel region of the other wearable electronic device according to the at least one appearance variable so that the adjusted appearance of the at least one non-panel region of any other wearable electronic device is adapted to the condition of the current environment.

In another aspect of the disclosure, a wearable electronic device is provided. The wearable electronic device can include at least one non-panel region having an electrically-adjustable appearance and a computation device. The at least one non-panel region can comprise a housing, a casing, a band, and/or a covering. The computation device can be configured to obtain at least one environment variable of the current environment of the wearable electronic device, and determine at least one appearance variable based on the at least one environment variable by referring to information about different appearances predetermined to be suitable for different environmental conditions; and generate a first control signal for adjusting the appearance of at least one non-panel region of the wearable electronic device according to the at least one appearance variable so that the adjusted appearance of the at least one non-panel region of the wearable electronic device is adapted to a condition of the current environment.

In some embodiments of the disclosure, the wearable electronic device further includes a display region configured to display frames provided by the computation device, and the computation device further obtains a plurality of appearances suitable for the condition of the current environment, and the display region displays a plurality of options respectively corresponding to the appearances on the display region of the wearable electronic device for selection by the user, and the computation device obtains the at least one user-selection variable according to the result of a selection made by the user.

In addition, the wearable electronic device may further include a detection device for detecting the current environment of the wearable electronic device, and the computation device obtains the at least one environment variable of the current environment of the wearable electronic device from the results of the detection. Moreover, the wearable electronic device may include a storage device for storing the different appearances predetermined to be suitable for different environmental conditions predefined by the user. Moreover, the wearable electronic device may include an image-capture device, capturing at least one image of the current environment, and the computation device further extracts the at least one environment variable from the captured image(s). Moreover, the wearable electronic device may include at least one sensor, sensing the current environment to obtain sensing data, and the computation device further extracts the at least one environment variable of the current environment from the sensing data. Furthermore, the wearable electronic device may include a connection-detection device for detecting whether at least one other wearable electronic device is connected to the wearable electronic device. The computation device may further generate a second control signal for adjusting the appearance of at least one non-panel region of the at least one another wearable electronic device according to the at least one appearance variable such so that the adjusted appearance of the at least one non-panel region of the other wearable electronic device is adapted to the condition of the current environment.

In the embodiments of the disclosure, the appearance of the non-panel region of the wearable device can be adjusted to suit, match, reflect, accommodate, or conform to (generally referred to as "adapt to" in the disclosure) detected conditions of different environments. In some embodiments, a symbolic meaning or a decorative or ornamental feature of the appearance of the wearable device can be adjusted to match corresponding features of the environment. Accordingly, the decorative or ornamental or accessory values of the wearable device can be enormously enhanced. Or the wearable device may convey more messages or become more expressive through varying appearances of non-panel regions. In addition, since different appearances can be predetermined to be suitable for different environments by a user and/or any database storing matching information, and the predetermined appearances may be updated by auto learning, the adjusted appearance can meet different design requirements and user demands/preferences more closely and more flexibly. In addition, since the appearance of the wearable device can be adjusted through a control signal generated in response to detection of the environment, the adjustment can be performed more easily and quickly.

Other aspects and features of the present invention will become apparent to those with ordinarily skill in the art upon review of the following descriptions of specific embodiments of the wearable electronic device and its operating method.

BRIEF DESCRIPTION OF DRAWINGS

The invention can be more fully understood by reading the subsequent detailed description and examples with references made to the accompanying drawings, wherein.

Corresponding numerals and symbols in the different figures generally refer to corresponding parts unless otherwise indicated. The figures are drawn to clearly illustrate the relevant aspects of the embodiments and are not necessarily drawn to scale.

DETAILED DESCRIPTION OF THE INVENTION

In order to illustrate the purposes, features and advantages of the invention, the embodiments and figures of the invention are shown in detail as follows. This description is made for the purpose of illustrating the general principles of the invention and should not be taken in a limiting sense. It should be understood that the embodiments may be realized in software, hardware, firmware, or any combination thereof.

In embodiments of the disclosure, at least one environment variable of a current environment of a wearable electronic device can be obtained. At least one appearance variable can then be determined based on the at least one environment variable by referring to information about different appearances predetermined to be suitable for different environmental conditions. A control signal can be generated for adjusting an appearance of at least one non-panel region of the wearable electronic device according to the at least one appearance variable. Accordingly, the adjusted appearance of the at least one non-panel region of the wearable electronic device can be adapted to a condition of the current environment.

Figure 1:
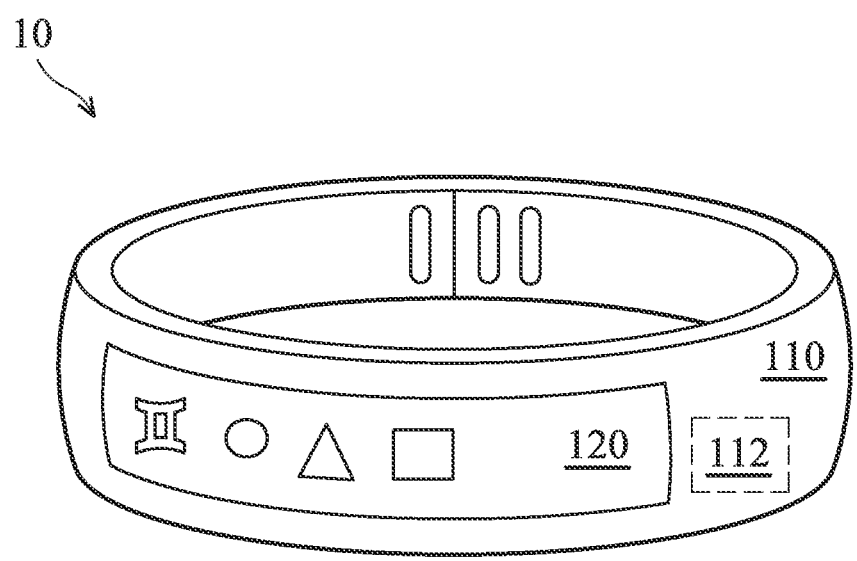
FIG. 1 is a schematic diagram illustrating the appearance of the wearable electronic device according to an embodiment of the invention.

FIG. 1 is a schematic diagram illustrating the appearance of the wearable electronic device 10 according to an embodiment of the invention. The wearable electronic device 10 is suitable to be worn on the user's body, such as wrist or head. The wearable electronic device 10 is exemplarily shown as a wristband in the embodiment shown by FIG. 1, but the disclosure is not limited thereto. For example, the wearable electronic device 10 can be any other types of wearable devices, such as glasses, watches, sport accessories and etc.

As shown in FIG. 1, the wearable electronic device 10 can include a non-panel region 110, at least one electronic device 112 and a display region 120. The display region 120 can be configured to display frames provided by a computation device (not shown) among the at least one electronic device 112. The display region 120 can be configured to display information content to be provided by the wearable electronic device 10 and/or any messages or contents that can enable operation, communication, or interaction by the user with the wearable electronic device 10. Moreover, the display region 120 may be a touch-sensitive display that can not only output information to the user but can also receive input from the user. In addition, the display region can be implanted by a display panel. For example, the display region 120 could include a touch display panel such as a resistive touch panel, a capacitive touch panel, an optical touch panel or an electromagnetic touch panel.

The non-panel region 110 can include a partial or whole region of the wearable electronic device 10 other than the display region 120 and the at least one electronic device 112. The non-panel region 110 may provide a mechanical function such as supporting and/or connecting different components of the wearable electronic device 10. In addition, the non-panel region 110 may provide a decorative or ornamental function. In different embodiments, the non-panel region 110 includes an housing, a casing, a band, and/or a covering of the wearable electronic device 10. In addition, the non-panel region can have an electrically-adjustable appearance. For example, the non-panel region can be implemented by one or more flexible display devices, electric paper (e-paper), and/or one or more LED lights, and any other types of electronic devices having electrically-adjustable appearances.

Additionally, the wearable electronic device 10 can include at least one electrical component 112. For example, the at least one electrical component 112 can include one or more computation devices, one or more storage devices, one or more connection detecting devices, one or more communication devices, and one or more environment detection devices, part or all of which can be separate from each other or integrated with each other. The one or more environment detection devices can include at least one image-capture device, a sensor (such as light sensor or color sensor, a temperature sensor, a humidity sensor), an barometer, an antenna, a GPS receiver, a wireless communication transceiver, a haptic device, an accelerometer, a speedometer, a health monitor, and/or any hardware/software device/module (a database or an application) capable of fetching or providing any environmental information, e.g., a current time/date/location/temperature information. In addition, the electrical component 112 can be disposed in any place of the wearable electronic device 10 to meet design requirements. The current environment of the wearable electronic device 10 can be detected by the one or more environment detection devices. In response to the detection, one or more characteristics of the appearance of the non-panel region 110 can be adjusted in correspondence with the current environment of the wearable electronic device 10, as will be explained more in the following disclosure.

Figure 2:
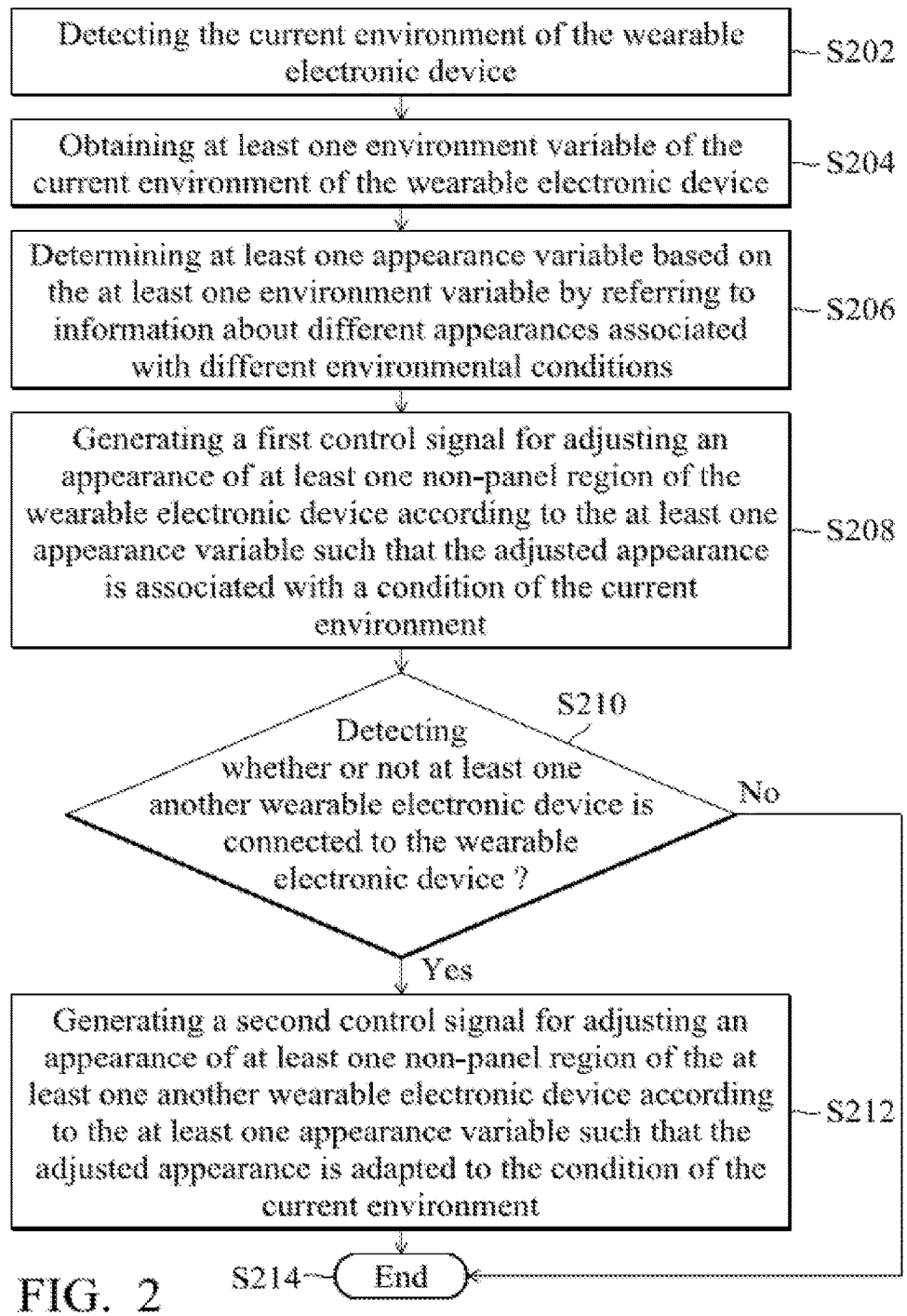
FIG. 2 is a flowchart illustrating an operating method for controlling a wearable electronic device according to an embodiment of the invention.

FIG. 2 is a flowchart illustrating an operating method for controlling a wearable electronic device according to an embodiment of the invention. The operating method can be utilized for controlling the wearable electronic device 10 in FIG. 1 but not limited thereto. It is noted the example flow may include one or more operations, actions, or functions as represented by one or more of blocks S202-S214. Although illustrated as discrete blocks, various blocks may be divided into additional blocks, combined into fewer blocks, or eliminated, depending on the desired implementation.

The flow may begin by step S202, where the current environment of the wearable electronic 10 is detected. In step S204, at least one environment variable of the current environment of the wearable electronic device 10 is obtained to represent the detection result. More specifically, the environment variable may include at least one temporal variable, at least one spatial/location variable, at least one light variable, at least one occasion variable, at least one user biological variable, and/or at least one air condition variable. For example, the temporal variable includes information about the date, time (such as a specific moment or a period of time), month and/or year. The spatial/location variable may indicate the current location of the user. The light variable may include the luminosity and/or the color of the environment. The occasion variable may indicate the type/occasion of the environment such as a working occasion (e.g., factory or a meeting room), a social occasion (e.g., a wedding ceremony), or a scenic spot. The user biological variable may include a physical biological parameter such as a blood pleasure or a heart rate. The air condition variable may include temperature, humidity and/or air quality.

In step S206, at least one appearance variable based on the environment variable is determined by referring to information about different appearances predetermined to be suitable for different environmental conditions. Afterwards, in step S208, a first control signal for adjusting the appearance of at least one non-panel region 110 of the wearable electronic device 10 is generated according to the appearance variable so that the adjusted appearance is adapted to a condition of the current environment.

In an embodiment where the environment variable includes an temporal variable, the temporal variable could be at least one specific date of one week or one month or a holiday, and the different appearances predetermined to be suitable for the different environmental conditions can include at least one preferred or suitable appearance predetermined to be associated with at least one specific date. For example, the appearance of the non-panel region 110 of the wearable electronic device 10 could be determined to be formal when the temporal variable indicates that it is a weekday, and the appearance of the non-panel region 110 of the electronic device 10 could be determined to be casual when the date indicates that it is the weekend.

In some embodiments, the flowchart may end after step 208 is finished. In some other embodiments, the flowchart may further comprise steps 210-S212. In step S210, whether or not at least one other wearable electronic device is connected to the wearable electronic device 10 is detected. If there is no another wearable electronic device connected to the wearable electronic device 10, step S214 is executed for ending the operating method. If there is another wearable electronic device connected to the wearable electronic device 10, step S212 is executed. In step S212, a second control signal for adjusting the appearance of at least one non-panel region of the at least one another wearable electronic device is generated according to the at least one appearance variable so that the adjusted appearance of the at least one non-panel region of the at least one another wearable electronic device is adapted to the condition of the current environment.

It is noted that S212 may utilize the environment the appearance variable determined in step S206. Alternatively or additionally, one or more additional steps similar to step S204 and/or S206 may be inserted between S210 and S212 for determine appearance variable for the other wearable electronic device. For example, a first environment variable can be obtained and a first appearance variable can be determined for the wearable electronic device 10. And the first environment variable and/or a second environment can be obtained and/or the first appearance variable and/or a second appearance variable can be obtained for the other wearable electronic device. Finally, step S214 can be executed for ending the operating method.

Furthermore, in some embodiments of step 206 and/or S212, the at least one appearance variable can be determined further based on the at least one non-environmental variable. For example, the at least one non-environmental variable comprises at least one user-selection variable. More specifically, one or more candidate appearances of either of the wearable electronic devices predetermined to be suitable for the condition of the current environment can be provided first. A plurality of options for suggesting the one or more candidate appearances can be displayed on a display region of the wearable electronic device to be selected by a user. A user-selection variable can be obtained according to the result of a selection made by the user. With such an implementation, the user can decide whether to accept the suggested appearance or can select from a plurality of candidate appearances. Accordingly, the adjustment of the appearance of the wearable electronic device can be more user-friendly and more flexible, and closer to user preference/demands.

Figure 3:
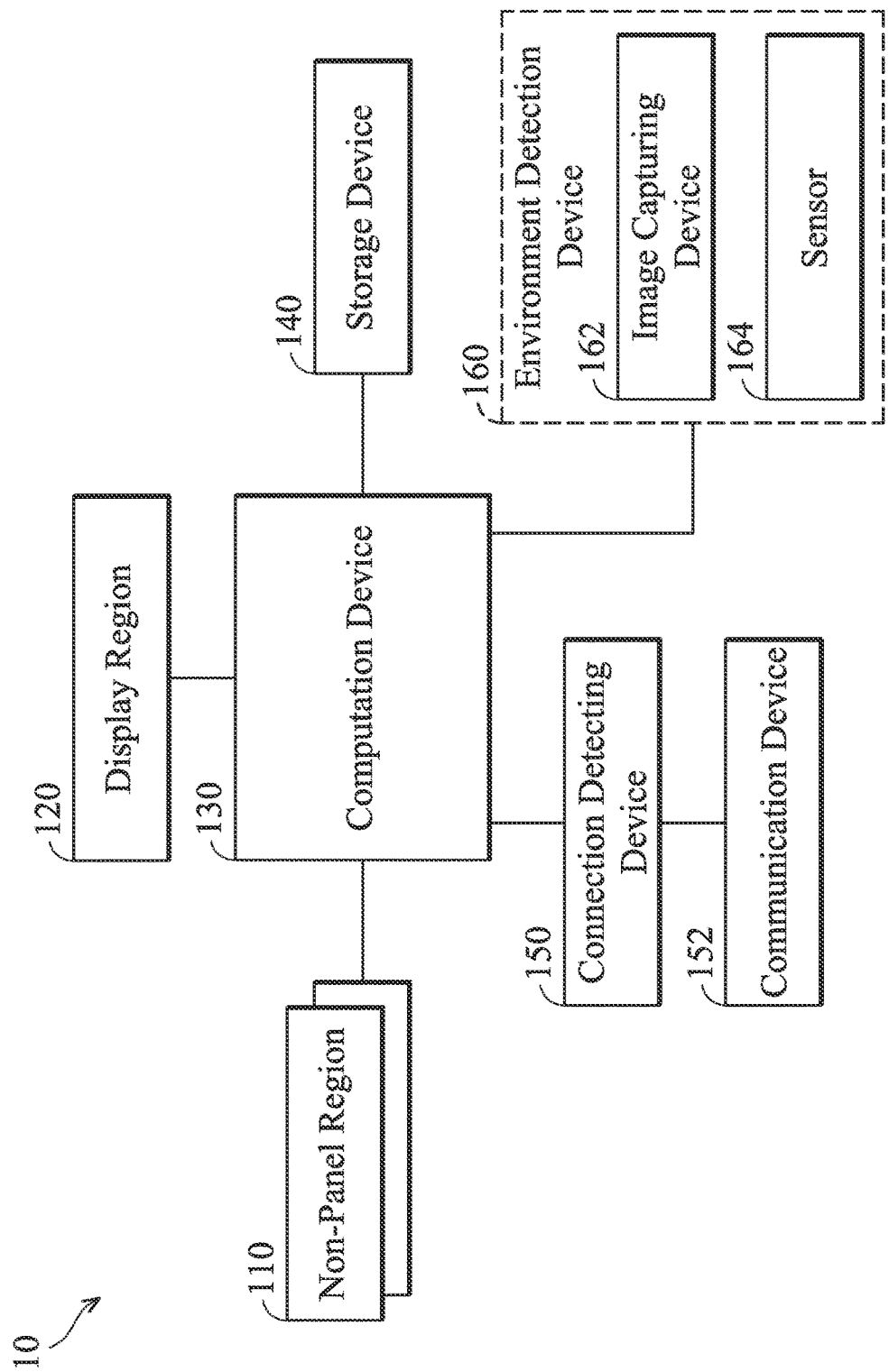
FIG. 3 is a schematic diagram illustrating the wearable electronic device according to an embodiment of the invention.

FIG. 3 is a schematic diagram of the wearable electronic device 10 according to an embodiment of the invention. The wearable electronic device 10 can include at least one non-panel region 110, a display region 120, and a computation device 130.

The computation device 130 can be configured to obtain at least one environment variable of the current environment of the wearable electronic device 10 and determine at least one appearance variable based on the environment variable by referring to information about different appearances predetermined to be suitable for different environmental conditions. In addition, the computation device 130 generates a first control signal for adjusting the appearance of at least one non-panel region 110 of the wearable electronic device 10 according to the at least one appearance variable so that the adjusted appearance of the at least one non-panel region 110 of the wearable electronic device 10 is adapted to a condition of the current environment. It is noted that a control circuit (not shown) can be configured to adjust the appearance of at least one non-panel region 110. The control circuit can be integrated as a part of the computing device 130 and provide at least one electrical output signal to adjust the appearance of the at least one non-panel region 110 in response to the first control signal. Alternatively, the control circuit can be disposed to be electrically coupled between the computing device 130 and the at least one non-panel region 110 and provide at least one electrical output signal to adjust the appearance of at least one non-panel region 110 in response output signal to adjust the appearance of the at least one non-panel region 110 in response to the first control signal.

Additionally, the wearable electronic device 10 can further include an environment detection device 160. The environment detection device 160 can detect the current environment of the wearable electronic device 10, and the computation device 130 obtains the at least one environment variable of the current environment of the wearable electronic device 10 from the result of the detection. Furthermore, the environment detection device 160 can include an image-capture device 162 and/or a sensor 164. For example, the image-capture device 162 could be a camera which includes lens, and the sensor 164 could include a light sensor, a color sensor, a biological sensor, a temperature sensor, a spatial/location sensor and/or an air condition sensor. In one embodiment, the image-capture device 162 is configured to capture at least one image of the current environment of the wearable electronic device 10, and the computation device 130 extracts the at least one environment variable from the captured image(s). In another embodiment, the sensor 164 detects and senses the current environment of the wearable electronic device 10 to obtain sensing data, and the computation device further extracts the at least one environment variable of the current environment from the sensing data. For example, the sensing data could include information about light, motion, temperature, magnetic fields, gravity, humidity, moisture, vibration, pressure, electrical fields, sound, and other physical aspects of the current environment of the wearable electronic device 10.

Furthermore, the wearable electronic device 10 can further include storage device 140. The storage device 140 can store different appearances predetermined to be suitable for different environmental conditions predefined by a user. For example, the storage device can store a look-up table which provides information about the different appearances predetermined to be suitable for different environmental conditions. The storage unit may include one or a plurality of random access memories (RAM), read-only memories (ROM), flash memories, cache memories and/or registers.

The wearable electronic device 10 can further include one or more of a connection detecting device 150 and a communication device 152. In some embodiments, the connection detecting device 150 is configured to detect whether at least one other wearable electronic device is connected to the wearable electronic device 10. If there is another wearable electronic device, the computation device 130 generates a second control signal for adjusting the appearance of at least one non-panel region of the at least one other wearable electronic device according to the at least one appearance variable. As such, the adjusted appearance of the at least one non-panel region of the at least one other wearable electronic device is adapted to the condition of the current environment. The second control signal can be transmitted with by wire or wirelessly. For example, they are transmitted wirelessly by a communication device 152 of the wearable electronic device 10 according to the protocol of wireless communication which constitutes GSM, GPRS, EDGE, UMTS, W-CDMA, TD-CDMA, Bluetooth, NFC, WiFi, WiMAX, LTE, LTE-A or TD-LTE. Therefore, the wearable electronic device 10 can not only adjust the appearance of its non-panel region 110 but also adjust the appearance of other non-panel regions of other wearable electronic devices for further suiting the current environment.

Figure 4A:
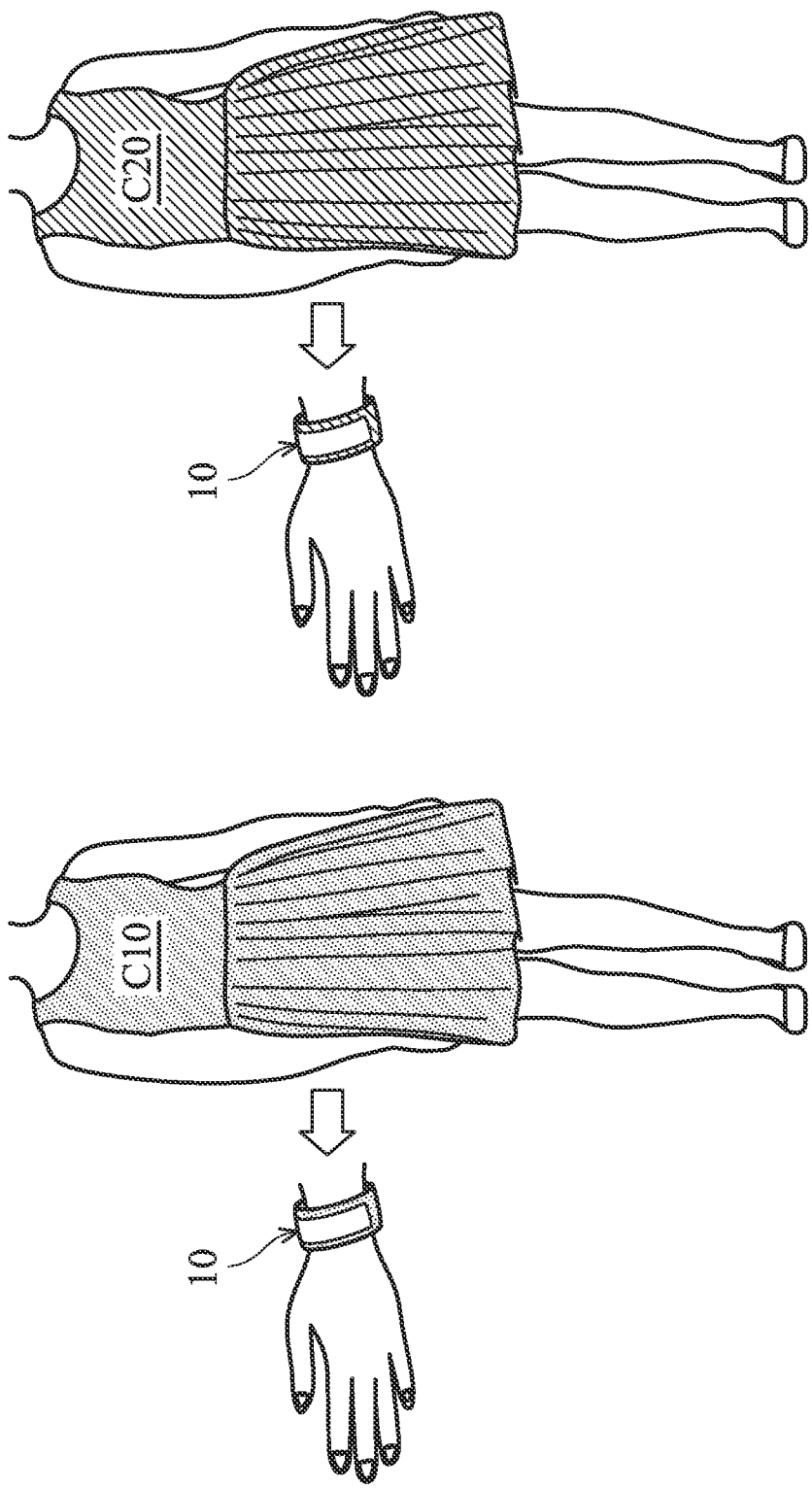
FIG. 4A is a schematic diagram illustrating how the appearance of a wearable electronic device can be adapted to clothing/accessory of a user according to an embodiment of the invention.

FIG. 4A is a schematic diagram illustrating how the appearance of a wearable electronic device can be adapted to clothing/accessory of a user according to an embodiment of the invention. FIG. 4A is explained with the wearable electronic device in FIG. 1 and FIG. 3 but not limited thereto. In this embodiment, the current environment of the wearable electronic device 10 could be detected by the image-capture device 162 or the sensor 164 illustrated in FIG. 3, and the at least one environment variable of the current environment of the wearable electronic device can be obtained from the results of the detection. The at least one environment variable comprises at least one clothing/accessory variable of the user. More specifically, the at least one clothing/accessory variable of the user comprises at least one color of the clothing/accessory of the user and/or at least one pattern of the clothing/accessory of the user. In addition, different appearances can be predetermined to be suitable for different colors and/or patterns of the user. The term "suitable" here can mean "matching." In other words, different appearances can be predetermined to match different colors of the clothing/accessory of the user and/or different clothing/accessory patterns of the user. For example, the color of the appearances of the non-panel region 110 and the color of the user clothing/accessory could be harmonious colors or belong to the same color system. For example, the color of the appearances of the non-panel region 110 and the color of the user clothing/accessory could be complementary colors or belong to opposite color systems. As such, the wearable electronic device 10 could match the clothing/accessory of the user so that they can conform to a specific style together. The style, for example, can be a fashion/retro style or a formal/casual style. In addition, the style may correspond to the preference of the user or a date/occasion that is special to the user, such as a birthday or a wedding anniversary.

In the embodiment shown in FIG. 4A, the wearable electronic device 10 can detect and obtain a clothing/accessory variable C10 or C20 which includes color and/or pattern information of the clothing/accessory currently or to be worn by the user, and the appearance of the non-panel region 110 of the wearable electronic device 10 can be adjusted in accordance with the clothing/accessory variable C10 or C20. Since the user does not need to put on another wearable device by himself or herself to match his/her clothing/accessory, the appearance of the wearable electronic device 10 can be matched to the clothing/accessory of the user in a more convenient way. In addition, the appearance of the non-panel region 110 can be determined according to various reference information for matching, which may be generated according to user preference/real-time selection, system suggestion (e.g., by referring to one or more matching databases, e.g., a fashion-trend database, a style database, and etc.), and/or auto-learning mechanism. Therefore, the appearance of the wearable electronic device 10 can be more closely and flexibly matched to the clothing/accessory of the user, in terms of user preference and/or user mood, and/or in a fashion angle.

Figure 4B:
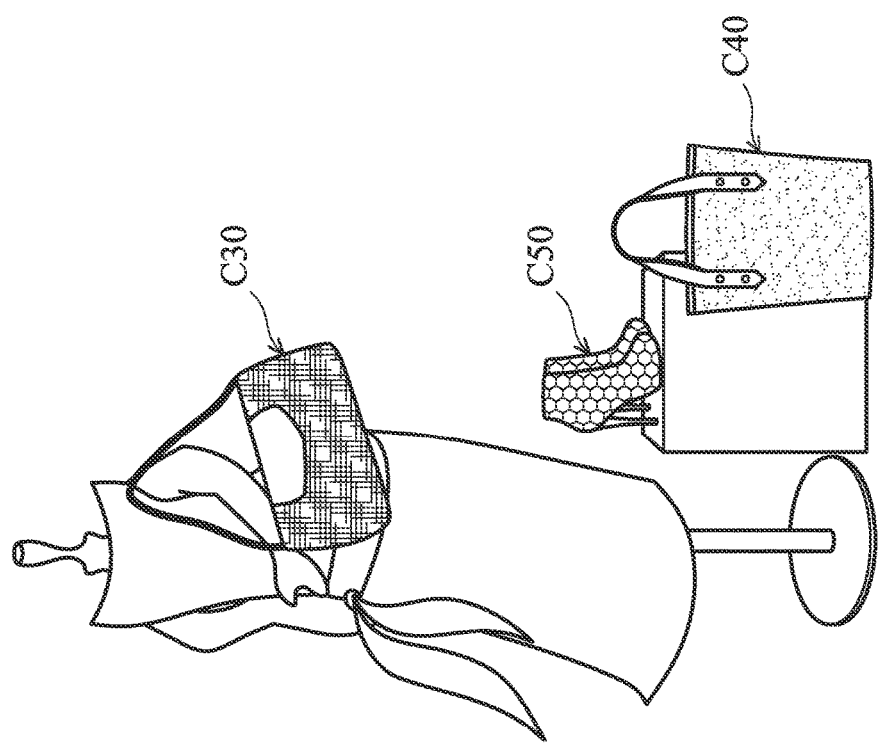
FIG. 4B is another schematic diagram illustrating how respective appearances of two wearable electronic devices can be adjusted according to an embodiment of the invention.

FIG. 4B is another schematic diagram illustrating how respective appearances of two wearable electronic devices can be adjusted according to an embodiment of the invention. The embodiment is explained with the wearable electronic device 10 of FIG. 1 and FIG. 3 and another wearable electronic device 20 but is not limited thereto. In some embodiments, the other wearable electronic device 20 is glasses, a watch, a sport accessory, or another wristband. However, as shown in FIG. 4B, the other wearable electronic device 20 could be any other types of accessory such as bags C30 and C40, shoes C50, scarf or earrings in some other embodiments.

In this embodiment, the connection detecting device 150 of the wearable electronic device 10 detects whether or not at least one other wearable electronic device 20 is connected to the wearable electronic device 10. When another wearable electronic device 20 is detected, the wearable electronic device 10 generates a second control signal for adjusting the appearance of at least one non-panel region of the at least one other wearable electronic device according to the at least one appearance variable so that the adjusted appearance of the at least one non-panel region of any other wearable electronic device is adapted to the condition of the current environment.

In a non-limiting example, the environment variable is one or more clothing/accessory variables of the clothing/accessory currently or to be worn by the user. The appearances of both of the wearable electronic device 10 and another wearable electronic device can be adjusted corresponding to the clothing/accessory. Therefore, not only does the appearance of the wearable electronic device 10 change, but also the appearance of the other electronic device 20 can change.

Figure 5:
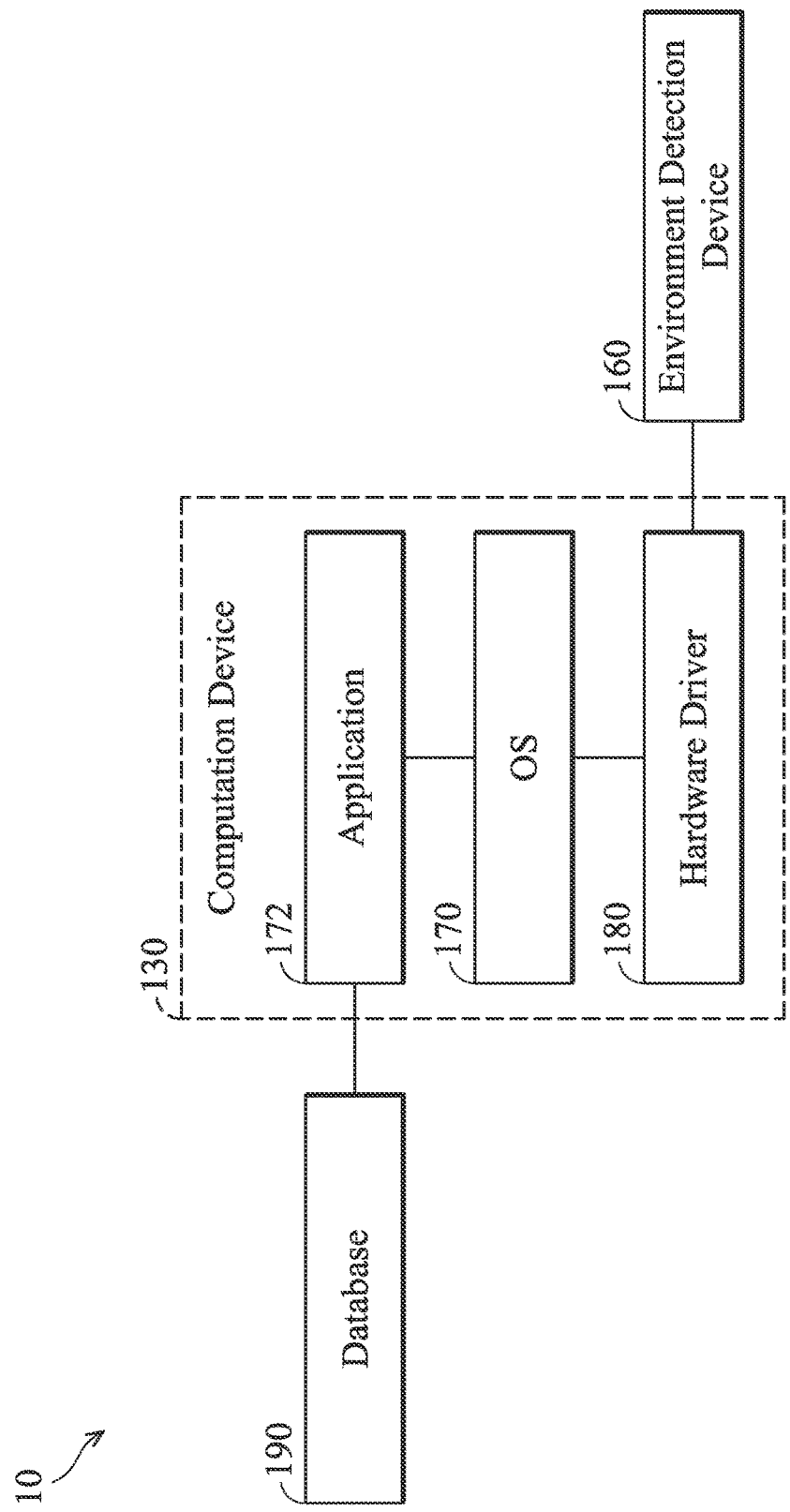
FIG. 5 is a schematic diagram illustrating a computation device in a wearable electronic device according to an embodiment of the invention.

FIG. 5 is a schematic diagram illustrating a computation device in a wearable electronic device according to an embodiment of the invention. The computation device can be implemented in the wearable electronic device 10 in FIG. 1 and implemented as the computation device 130 but is not limited thereto. The computation device 130 can execute an operating system (OS) 170, an application 172 and a hardware driver 180. The hardware driver 180 can be configured to drive the hardware components of the wearable electronic device 10 such as the environment detection device 160. In one embodiment, the environment detection device 160 detects the current environment of the wearable electronic device 10 and transmits the detected result to the hardware drivers 180. The hardware driver 180 transmits the detected result to the OS 170, and the application 172 obtains the detected result for setting the appearance of the at least one non-panel region 110. Afterwards, a control signal can be generated by the OS 170 in response to the detection result of the application 172 and provided to adjust the appearance of the non-panel region 110 of the wearable electronic device 10. Therefore, the computation device 130 can obtain the environment variable, determine the appearance variable, and generate the first control signal for adjusting the appearance of the non-panel region 110 accordingly.

It is noted that in determination of the suitable appearance of the non-panel region, the application 172 may obtain reference information from a database 190. Preferably but not limitedly, the reference information of the database 190 includes predefined information for matching, and the appearance variable can be determined by the application 172 based on the environmental variable in reference to the predefined information in the database 190.

The information could be predefined by the user, which means that the different appearances predetermined to be suitable for different environmental conditions can be determined by the user in advance. For example, the user can determine his/her favorite color and pattern as an appearance variable and stores the user-determined appearance variable in the data base. Accordingly, when the environment variable indicates a specific date such as a birthday of the user is obtained, the user-determined appearance variable of his/her favorite color and pattern can be suggested by the database 190. Moreover, the database 190 may include at least one look-up table, and the different appearances predetermined to be suitable for different environmental conditions can be obtained from the at least one look-up table.

In some embodiments, the database 190 is embedded with an auto-learning mechanism, and the information defining the different appearances predetermined to be suitable for the different environmental conditions can be updated by the auto-learning mechanism. More specifically, the selection and/or the preference of the user are recorded and analyzed statistically to update contents of the database 190. The update contents of the database may more closely reflect individual preference of the user. When the environment variable is obtained, the database 190 can provide and suggest the appearance variable based on the updated information in the database 190. For example, the user may often select a specific color and/or pattern on Saturday evenings, which can be recorded in the auto-learning database 190. As such, the specific color and/or pattern could be suggested automatically by the auto-learning database 190 when the obtained environment variable indicates that it is Saturday evening.

Figure 6:
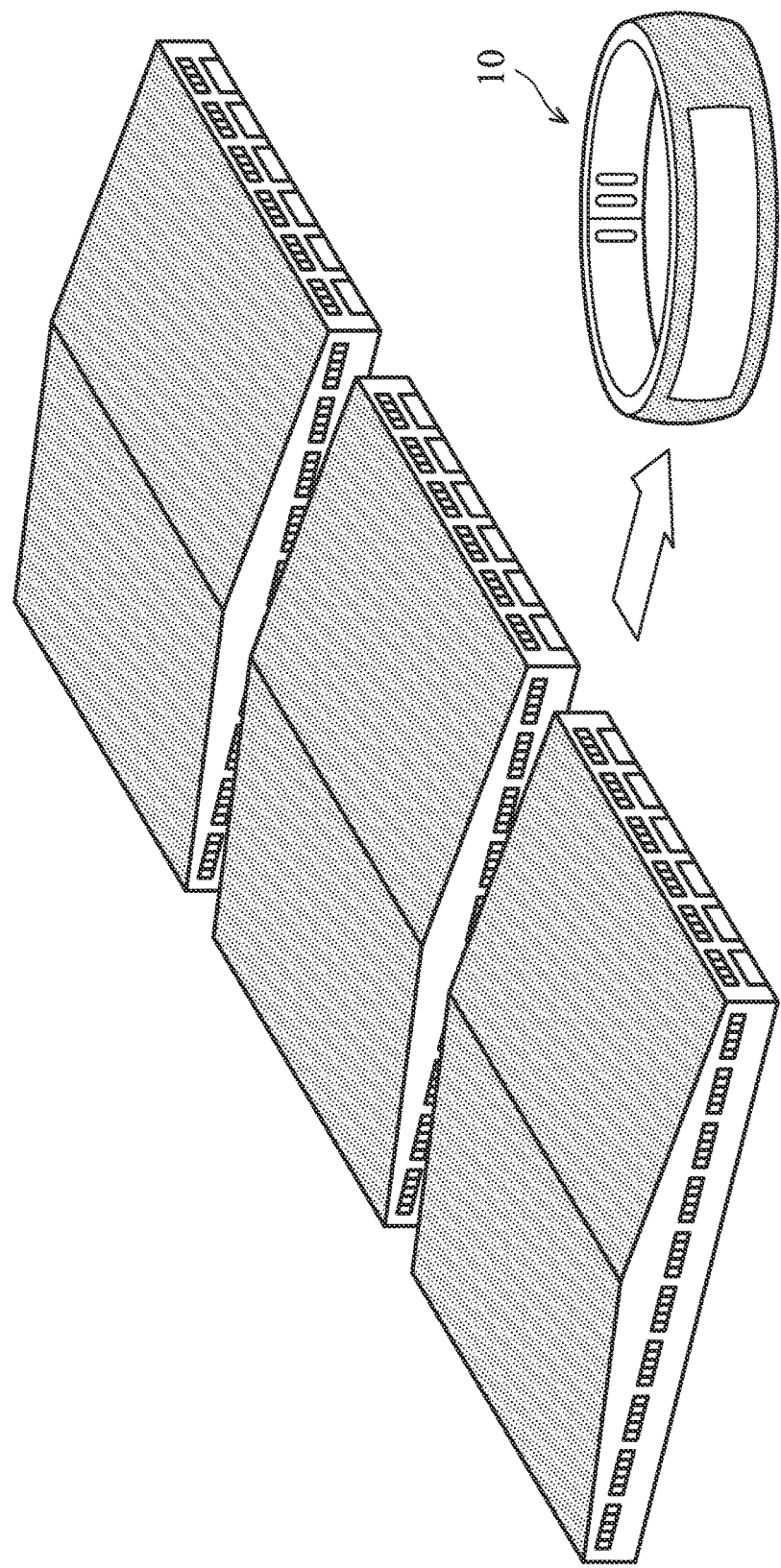
FIG. 6 is a schematic diagram illustrating how a wearable electronic device can be adjusted to adapt to an occasion according to an embodiment of the invention.

FIG. 6 is a schematic diagram illustrating how a wearable electronic device can be adjusted to adapt to an occasion according to an embodiment of the invention. The wearable electronic device 10 in FIG. 1 is used in the embodiment for explanation but the disclosure is not limited thereto. In the embodiment, the at least one environment variable comprises at least one social occasion variable. In addition, different appearances of non-panel region 110 can be predetermined to be suitable for different environmental conditions. The different appearances of the non-panel region 110 can comprise different colors and/or patterns suitable for different social occasions. The non-panel region 110 of the wearable electronic device 10 can be adjusted so that the appearance of the wearable electronic device 10 is appropriately matched to the occasion.

As shown in FIG. 6, the color and/or pattern of the non-panel region 110 of the wearable electronic device 10 may reflect the social occasion that the user is attending. For example, if the social occasion variable indicates that the wearable electronic device 10 is being worn at a wedding ceremony, the appearance of the wearable electronic device 10 could be adjusted to a color and/or pattern appropriate for a joyous atmosphere. If the social occasion variable indicates that the wearable electronic device 10 is being worn at a funeral, the appearance of the wearable electronic device 10 could be adjusted to a color and/or pattern that is appropriate for a solemn atmosphere. In addition, if the social occasion variable indicates that the wearable electronic device 10 is being worn in a dangerous location such as a factory 600 or a construction site, the appearance of the wearable electronic device 10 could be adjusted to a bright, vivid color and/or pattern so that it can easily be seen. In this regard, FIG. 6 shows three different generic drawings of buildings; one representing a wedding chapel, one representing a funeral home, and one representing a factory. A single arrow is shown between these buildings and the wearable electronic device 10. This arrow represents that the environmental variable of each of the buildings uniquely impacts the wearable device 10.

In another embodiment, an operating method for controlling a wearable electronic device may include sensing the current environment by at least one sensor to obtain sensing data, and extracting the environment variable of the current environment from the sensing data. In a non-limiting example, the environment variable comprises at least one environment brightness variable. Afterwards, the appearance variable can be determined based on the environmental variable to adjust the appearance of the wearable electronic device 10. The determination may be made by referring to a database. In one embodiment, different appearances can be predetermined to be suitable for different environment brightness values. For example, when the user is riding a bicycle or running outside and the detected environment brightness variable indicates that the brightness is at a low level, it could mean that the weather is cloudy or it is evening or night. As such, the appearance could be further adjusted to a higher contrast or a brighter color for increasing visibility and safety.

Figure 7:
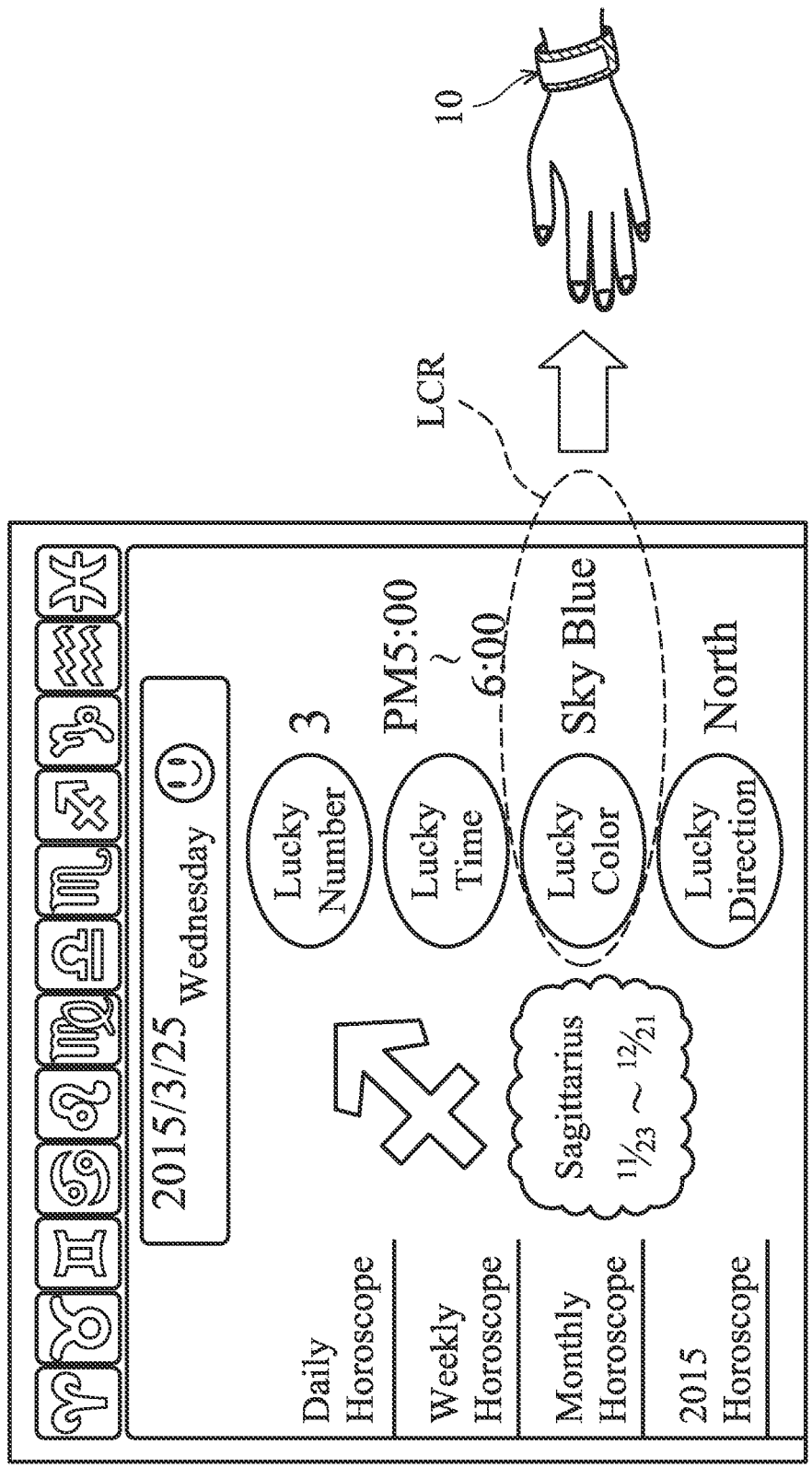
FIG. 7 is a schematic diagram illustrating how the appearance of a wearable electronic device can be adjusted to conform to a daily horoscope according to an embodiment of the invention.

FIG. 7 is a schematic diagram illustrating how the appearance of a wearable electronic device can be adjusted to conform to a daily horoscope according to an embodiment of the invention. The wearable electronic device 10 in FIG. 1 is referred to here for explanation but the disclosure is not limited thereto. In the embodiment, different lucky colors of the non-panel region 110 can be predetermined to be suitable for different dates or time periods, which for example, may be determined according to birth information (e.g., the birthday, birth month, or birth year) of the user. As shown in FIG. 7, daily horoscope information indicating different lucky number/time/color/direction for different horoscopes can be referred to by the wearable electronic device 10 to obtain different lucky color LCR on different dates and/or at different times for the user. The birth information including birthday, birth month and/or birth year of the user can be stored in the database 190. Different lucky colors can then be obtained on different dates and/at different times by referring to the daily horoscope information applying the horoscope of the user indicated by the birth information of the user. As such, the lucky color LCR can be suggested to the user on different dates and/at different times, and the user can determine whether or not to accept the lucky color suggestion for adjusting the appearance of the wearable electronic device 10.

In some embodiments, the at least one environmental variable include a user biological variable. The user biological variable may include a physical biological parameter such as a blood pleasure or a heart rate and may be obtained according to detection by a health monitor. The adjusted appearance of the wearable electronic device can reflect a mood or a health condition of the user or convey different messages. For example, the adjusted appearance may be predetermined by the user to be a specific color indicating his bad mood or another specific color to indicate his good mood. Alternatively, the adjusted appearance may be predetermined by the user to be a specific color indicating his bad condition or another specific color indicating his good health condition. And the adjusted appearance may also carry an alarming message (e.g., specific color or pattern) when the user is detected to be in a bad health condition. Moreover, the adjusted appearance may be obtained with reference to a health database/application capable of analyzing the health condition of the user or utilizing an analyzed result of the health condition of the user.

Furthermore, a combination of different environment variables can be obtained to determine a suitable appearance of the non-panel region of the wearable electronic device. For example, a speed meter/timer can detect running information (e.g., speed, run time, and/or run distance) of a running user and at the same time, a health monitor can detect a health condition (e.g., heart rate) of the running user. And the adjusted appearance of the wearable electronic device can more informatively reflect the detection of the different environment variables. For example, the non-panel region of the wearable electronic device can be adjusted to have an encouraging appearance when it is detected that the runner slows down his speed, an applause appearance when it is detected that the runner achieves a certain distance or has a health-benefiting heart rate, or an alarming appearance (e.g., red color) when it is detected that the runner has an excessively-high heart rate. More details can be analogized form the other embodiments of the disclosure, thus omitted here for brevity.

An embodiment of the disclosure also provides a non-transitory storage medium or a computer-readable recording medium. The non-transitory storage medium records at least one program instruction or program code. After being loaded into an electronic device with a screen, the at least one program instruction or program code is executed to carry out the method provided by each embodiment described above.

For example, after the at least one program instruction or program code in the computer-readable recording medium is loaded into the wearable electronic device 10 illustrated in FIG. 1 or FIG. 3, the wearable electronic device 10 runs the at least one program instruction or program code to execute the method provided by one of the embodiments described above. The computer-readable recording medium may be implemented as the storage device 140 in FIG. 3 or another memory accessible to the computation device 130 in FIG. 3. The computer-readable recording medium may be a read-only memory (ROM), a random-access memory (RAM), a CD-ROM, a tape, a floppy disk, or an optical data storage device.

Various functional components or blocks have been described herein. As will be appreciated by persons skilled in the art, the functional blocks will preferably be implemented through circuits (either dedicated circuits, or general purpose circuits, which operate under the control of one or more processors and coded instructions), which will typically comprise transistors that are configured in such a way as to control the operation of the circuitry in accordance with the functions and operations described herein. As will be further appreciated, the specific structure or interconnections of the transistors will typically be determined by a compiler, such as a register transfer language (RTL) compiler. RTL compilers operate upon scripts that closely resemble assembly language code, to compile the script into a form that is used for the layout or fabrication of the ultimate circuitry. Indeed, RTL is well known for its role and use in the facilitation of the design process of electronic and digital systems.

In the embodiments of the disclosure, the appearance of the non-panel region of the wearable device can be adjusted to suit, match, reflect, accommodate, or conform to (generally referred to as "adapt to" in the disclosure) detected conditions of different environments. In some embodiments, a symbolic meaning or a decorative or ornamental feature of the appearance of the wearable device can be adjusted to match corresponding features of the environment. Accordingly, the decorative or ornamental or accessory values of the wearable device can be enormously enhanced. Or the wearable device may convey more messages or become more expressive through varying appearances of non-panel regions. In addition, since different appearances can be predetermined to be suitable for different environments by a user and/or any database storing matching information, wherein the predetermined appearances may be updated by auto learning, the adjusted appearance can meet different design requirements and user demands/preferences more closely and more flexibly. In addition, since the appearance of the wearable device can be adjusted through a control signal generated in response to detection of the environment, the adjustment can be performed more easily and quickly.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term) to distinguish the claim elements.

While the invention has been described by way of example and in terms of the preferred embodiments, it is to be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An operating method for controlling a wearable electronic device, comprising:
   obtaining at least one environment variable of a current environment of the wearable electronic device;
   determining at least one appearance variable based on the at least one environment variable by referring to information about different appearances predetermined to be suitable for different environmental conditions;
   generating a first control signal for adjusting an electrically-adjustable appearance of at least one non-panel region of the wearable electronic device according to the at least one appearance variable so that the adjusted appearance of the at least one non-panel region of the wearable electronic device is adapted to a condition of the current environment;
   detecting whether or not at least one other wearable electronic device is connected to the wearable electronic device; and generating a second control signal for adjusting an appearance of at least one non-panel region of the at least one other wearable electronic device according to the at least one appearance variable so that the adjusted appearance of the at least one non-panel region of the at least one other wearable electronic device is adapted to the condition of the current environment.

2. The operating method as claimed in claim 1, wherein the at least one environment variable comprises at least one temporal variable, at least one spatial/location variable, at least one light variable, at least one occasion variable, at least one user biological variable, and/or at least one air condition variable.

3. The operating method as claimed in claim 2, wherein the at least one temporal variable comprises a date variable, a time variable, a year variable, a month variable, and a day variable.

4. The operating method as claimed in claim 2, wherein the different appearances predetermined to be suitable for the different environmental conditions comprises at least one preferred or suitable appearance predetermined to be suitable for at least one specific date.

5. The operating method as claimed in claim 2, wherein the different appearances predetermined to be suitable for the different environmental conditions comprise different lucky colors predetermined to be suitable for different dates or time periods determined according to a birthday, a birth month, or a birth year of a user.

6. The operating method as claimed in claim 1, wherein the at least one environment variable comprises at least one clothing/accessory variable of a user.

7. The operating method as claimed in claim 6, wherein the at least one clothing/accessory variable of the user comprises at least one color of clothing/accessory of the user and/or at least one pattern of clothing/accessory of the user.

8. The operating method as claimed in claim 7, wherein the different appearances predetermined to be suitable for the different environmental conditions comprise different colors and/or patterns matching different colors of clothing/accessory of the user and/or different clothing/accessory patterns of the user.

9. The operating method as claimed in claim 1, wherein the at least one environment variable comprises at least one social occasion variable.

10. The operating method as claimed in claim 9, wherein the different appearances predetermined to be suitable for the different environmental conditions comprise different colors and/or patterns suitable for different social occasions.

11. The operating method as claimed in claim 1, wherein the at least one environment variable comprises at least one environment brightness variable.

12. The operating method as claimed in claim 11, wherein the different appearances predetermined to be suitable for the different environmental conditions comprise different contrasts suitable for different environment brightness values.

13. The operating method as claimed in claim 1, wherein the step of determining the at least one appearance variable is further based on at least one non-environmental variable.

14. The operating method as claimed in claim 13, wherein the at least one non-environmental variable comprises at least one user-selection variable.

15. The operating method as claimed in claim 14, further comprising:
providing one or more candidate appearances to be suitable for the condition of the current environment;
displaying a plurality of options for suggesting the one or more candidate appearances on a display region of the wearable electronic device for selection by a user; and
obtaining the at least one user-selection variable according to a selection result made by the user.

16. The operating method as claimed in claim 1, further comprising detecting the current environment of the wearable electronic device, wherein the at least one environment variable of the current environment of the wearable electronic device is obtained from a result of the detection.

17. The operating method as claimed in claim 1, wherein the different appearances predetermined to be suitable for different environmental conditions are predefined by a user.

18. The operating method as claimed in claim 1, wherein the different appearances predetermined to be suitable for different environmental conditions are obtained from a look-up table.

19. The operating method as claimed in claim 1, wherein the information defining the different appearances predetermined to be suitable for the different environmental conditions is updated by an auto-learning mechanism.

20. The operating method as claimed in claim 1, wherein the step of obtaining the at least one environment variable of the current environment of the wearable electronic device comprises:
capturing at least one image of the current environment; and
extracting the at least one environment variable from the at least one image that was captured.

21. The operating method as claimed in claim 1, wherein the step of obtaining the at least one environment variable of the current environment of the wearable electronic device comprises:
sensing the current environment by at least one sensor to obtain sensing data; and
extracting the at least one environment variable of the current environment from the sensing data.

22. A wearable electronic device, comprising:
at least one non-panel region with an electrically-adjustable appearance;
a computation device, configured to obtain at least one environment variable of a current environment of the wearable electronic device, and determine at least one appearance variable based on the at least one environment variable by referring to information about different appearances predetermined to be suitable for different environmental conditions, and generate a first control signal for adjusting the electrically-adjustable appearance of at least one non-panel region of the wearable electronic device according to the at least one appearance variable so that the adjusted appearance of the at least one non-panel region of the wearable electronic device is adapted to a condition of the current environment; and
a connection-environment detection device, detecting whether at least one other wearable electronic device is connected to the wearable electronic device, wherein the computation device further generates a second control signal for adjusting an appearance of at least one non-panel region of the at least one other wearable electronic device according to the at least one appearance variable so that the adjusted appearance of the at least one non-panel region of the at least one other wearable electronic device is adapted to the condition of the current environment.

23. The wearable electronic device as claimed in claim 22, wherein the at least one environment variable comprises at least one temporal variable, at least one spatial/location variable, at least one light variable, at least one occasion variable, user biological variable, and/or at least one air condition variable.

24. The wearable electronic device as claimed in claim 22, wherein the at least one environment variable comprises at least one temporal variable.

25. The wearable electronic device as claimed in claim 24, wherein the at least one temporal variable comprises a date variable, a time variable, a year variable, a month variable, and a day variable.

26. The wearable electronic device as claimed in claim 24, wherein the different appearances predetermined to be suitable for the different environmental conditions comprise at least one preferred or suitable appearance predetermined to be suitable for at least one specific date.

27. The wearable electronic device as claimed in claim 22, wherein the different appearances predetermined to be suitable for the different environmental conditions comprise different lucky colors predetermined to be suitable for different dates or time periods determined according to a birthday, a birth month, or a birth year of a user.

28. The wearable electronic device as claimed in claim 22, wherein the at least one environment variable comprises at least one clothing/accessory variable of a user.

29. The wearable electronic device as claimed in claim 28, wherein the at least one user's clothing/accessory variable comprises at least one color of clothing/accessory of a user and/or at least one pattern of clothing/accessory of the user.

30. The wearable electronic device as claimed in claim 29, wherein the different appearances predetermined to be suitable for the different environmental conditions comprise different colors and/or patterns matching different colors of clothing/accessory of the user and/or different patterns of clothing/accessory of the user.

31. The wearable electronic device as claimed in claim 22, wherein the at least one environment variable comprises at least one social occasion variable.

32. The wearable electronic device as claimed in claim 31, wherein the different appearances predetermined to be suitable for the different environmental conditions comprise different colors and/or patterns suitable for different social occasions.

33. The wearable electronic device as claimed in claim 22, wherein the at least one environment variable comprises at least one environment brightness variable.

34. The wearable electronic device as claimed in claim 33, wherein the different appearances predetermined to be suitable for the different environmental conditions comprise different contrasts suitable for different environment brightness values.

35. The wearable electronic device as claimed in claim 22, wherein the computation device determines the at least one appearance variable further based on at least one non-environmental variable.

36. The wearable electronic device as claimed in claim 35, wherein the at least one non-environmental variable comprises at least one user-selection variable.

37. The wearable electronic device as claimed in claim 36, further comprising a display region, and the computation device further provides one or more candidate appearances to be suitable for the condition of the current environment, and the display region displays a plurality of options for suggesting the one or more candidate appearances on a display region of the wearable electronic device to be selected by a user; and the computation device obtains the at least one user-selection variable according to a selection result made by the user.

38. The wearable electronic device as claimed in claim 22, further comprising a environment detection device, detecting the current environment of the wearable electronic device, and the computation device obtains the at least one environment variable of the current environment of the wearable electronic device from a result of the detection.

39. The wearable electronic device as claimed in claim 22, further comprising a storage device, storing the different appearances predetermined to be suitable for different environmental conditions predefined by a user.

40. The operating method as claimed in claim 22, wherein the different appearances predetermined to be suitable for different environmental conditions are obtained from a look-up table.

41. The wearable electronic device as claimed in claim 22, wherein the information defining the different appearances predetermined to be suitable for the different environmental conditions is updated by an auto-learning mechanism.

42. The wearable electronic device as claimed in claim 22, further comprising
an image-capture device, capturing at least one image of the current environment; and
the computation device further extracts the at least one environment variable from the at least one image that was captured.

43. The wearable electronic device as claimed in claim 22, further comprising
at least one sensor, sensing the current environment to obtain sensing data; and
the computation device further extracts the at least one environment variable of the current environment from the sensing data.

44. The wearable electronic device as claimed in claim 22, wherein the at least one environmental variable comprises at least one user biological variable.

45. The wearable electronic device as claimed in claim 22, wherein the at least one user biological variable comprises at least one user psychological characteristics variable and/or at least one user physiological characteristics variable.

46. The wearable electronic device as claimed in claim 45, wherein the different appearances predetermined to be suitable for the different environmental conditions comprise different colors and/or patterns reflecting different mental conditions and/or physical conditions of the user.

47. The wearable electronic device as claimed in claim 22, wherein the at least one non-panel region comprises a housing, a casing, a band, and/or a covering.

48. The wearable electronic device as claimed in claim 22, further comprising at least one display region, configured to display frames provided by the computation device.

* * * * *